United States Patent
Oneda et al.

(10) Patent No.: US 9,295,377 B2
(45) Date of Patent: Mar. 29, 2016

(54) ENDOSCOPE WITH IMAGING CAPSULE

(75) Inventors: Katsumi Oneda, Alpine, NJ (US); Ron Hadani, Cresskill, NJ (US)

(73) Assignee: COGENTIX MEDICAL, INC., Minnetonka, MN (US)

( * ) Notice: Subject to any disclaimer, the term of this patent is extended or adjusted under 35 U.S.C. 154(b) by 1642 days.

(21) Appl. No.: 12/224,051

(22) PCT Filed: Feb. 14, 2007

(86) PCT No.: PCT/IL2007/000204
§ 371 (c)(1),
(2), (4) Date: Jul. 13, 2010

(87) PCT Pub. No.: WO2007/093994
PCT Pub. Date: Aug. 23, 2007

(65) Prior Publication Data
US 2010/0298640 A1    Nov. 25, 2010

Related U.S. Application Data

(60) Provisional application No. 60/773,932, filed on Feb. 16, 2006, provisional application No. 60/806,162, filed on Jun. 29, 2006.

(51) Int. Cl.
*A61B 1/06* (2006.01)
*A61B 1/00* (2006.01)
(Continued)

(52) U.S. Cl.
CPC .............. *A61B 1/053* (2013.01); *A61B 1/00029* (2013.01); *A61B 1/00071* (2013.01);
(Continued)

(58) Field of Classification Search
CPC ........... A61B 1/00105; A61B 1/00071; A61B 1/0008; A61B 1/00096; A61B 1/00101; A61B 1/05; A61B 1/053; A61B 1/0661; A61B 1/0676; A61B 1/0684; A61B 1/0692
USPC .......... 600/109, 112, 114, 160, 172, 175, 122, 600/136
See application file for complete search history.

(56) References Cited

U.S. PATENT DOCUMENTS 5,643,175 A    7/1997 Adair
5,846,183 A  * 12/1998 Chilcoat ............ A61B 1/00142
                                                    600/112
(Continued)

FOREIGN PATENT DOCUMENTS

WO    WO 9315648 A1 *  8/1993 ......... A61B 1/00052
WO    WO 2005/115221   12/2005
WO    WO 2006/001377    1/2006

OTHER PUBLICATIONS

Communication Under Rule 71(3) EPC Dated Dec. 12, 2012 From the European Patent Office Re. Application No. 07706146.3.
(Continued)

*Primary Examiner* — Anhtuan T Nguyen
*Assistant Examiner* — William Chou
(74) *Attorney, Agent, or Firm* — Barbara A. Wrigley; Fox Rothschild LLP

(57) ABSTRACT

A method of examining internal body portions of patients. The method includes providing an imaging capsule including an image capturing unit, mounting the imaging capsule on a first elongate tube suitable for insertion into a body cavity, in a manner which prevents release of the imaging capsule from the first elongate tube within a body cavity, inserting the first elongate tube with the capsule mounted thereon into a patient, retracting the first elongate tube from the patient, separating the imaging capsule from the first elongate tube, disposing of the first elongate tube, mounting the imaging capsule on a second elongate tube and inserting the second elongate tube with the imaging capsule mounted thereon into a patient.

38 Claims, 6 Drawing Sheets

(51) Int. Cl.
*A61B 1/04* (2006.01)
*A61B 1/05* (2006.01)

(52) U.S. Cl.
CPC ......... *A61B1/00105* (2013.01); *A61B 1/00016* (2013.01); *A61B 1/00032* (2013.01); *A61B 1/0684* (2013.01); *A61B 2560/0219* (2013.01)

(56) References Cited

U.S. PATENT DOCUMENTS

| | | | | |
|---|---|---|---|---|
| 6,632,171 | B2* | 10/2003 | Iddan et al. | 600/106 |
| 8,827,899 | B2* | 9/2014 | Farr | A61B 1/00052 600/188 |
| 2001/0051766 | A1* | 12/2001 | Gazdzinski | 600/309 |
| 2003/0120130 | A1* | 6/2003 | Glukhovsky et al. | 600/109 |
| 2004/0267095 | A1* | 12/2004 | Miyake et al. | 600/175 |
| 2005/0165272 | A1* | 7/2005 | Okada et al. | 600/114 |
| 2005/0182299 | A1* | 8/2005 | D'Amelio et al. | 600/175 |
| 2005/0277808 | A1 | 12/2005 | Sonnenschein et al. | |
| 2006/0020171 | A1 | 1/2006 | Gilreath | |
| 2006/0217594 | A1* | 9/2006 | Ferguson | 600/175 |
| 2009/0326328 | A1* | 12/2009 | Kucklick | 600/175 |
| 2011/0028790 | A1* | 2/2011 | Farr | A61B 1/00052 600/187 |

OTHER PUBLICATIONS

Communication Under Rule 71(3) EPC Dated Mar. 28, 2013 From the European Patent Office Re. Application No. 07706146.3.
Communication Pursuant to Rules 70(2) and 70a(2) EPC Dated Apr. 26, 2011 From the European Patent Office Re. Application No. 07706146.3.
Supplementary European Search Report and the European Search Opinion Dated Apr. 7, 2011 From the European Patent Office Re. Application No. 07706146.3.
Response Dated Oct. 26, 2011 to Communication Pursuant to Rules 70(2) and 70a(2) EPC of Apr. 26, 2011 From the European Patent Office Re. Application No. 07706146.3.
International Preliminary Report on Patentability Dated Jan. 22, 2009 From the International Bureau of WIPO Re.: Application No. PCT/IL2007/000204.
International Search Report Dated Sep. 8, 2008 From the International Searching Authority Re.: Application No. PCT/IL07/00204.
Written Opinion Dated Sep. 8, 2008 From the International Searching Authority Re.: Application No. PCT/IL07/00204.
Communication Pursuant to Article 94(3) EPC Dated Nov. 28, 2011 From the European Patent Office Re. Application No. 07706146.3.

* cited by examiner

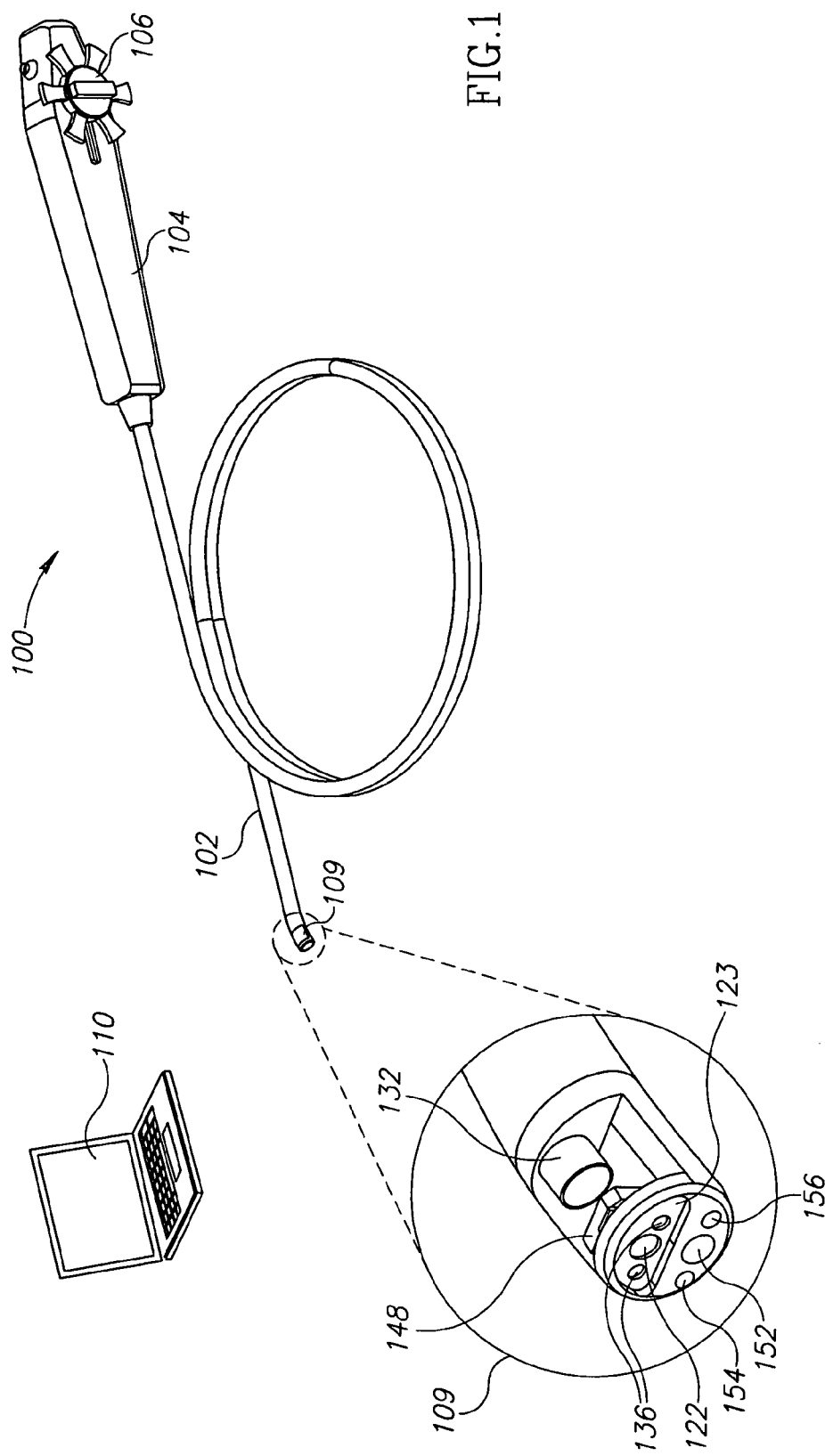

ENDOSCOPE WITH IMAGING CAPSULE

RELATED APPLICATIONS

This application is a National Phase of PCT Patent Application No. PCT/IL2007/000204 having International filing date of Feb. 14, 2007, which claims the benefit under 119(e) of US Provisional Patent Application 60/773,932, filed on Feb. 16, 2006 and of US Provisional Patent Application 60/806,162, filed on Jun. 29, 2006, the disclosures of which are incorporated herein by reference.

FIELD OF THE INVENTION

The present invention relates to endoscopes and particularly to endoscopes having disposable parts.

BACKGROUND OF THE INVENTION

Endoscopes are used to view internal tissue of humans, and for many other tasks. Endoscopes are used to acquire high quality images, and allow access to body tissue for taking biopsy samples, delivery of therapeutic means and/or introduction of fluids. It is desired to allow easy maintenance and sterilization of endoscopes.

U.S. Pat. No. 4,895,138 to Yabe, the disclosure of which is incorporated herein by reference, describes an endoscope having an imaging unit at its distal end, which is designed to be replaceable by a technician for ease of maintenance.

U.S. patent publication 2004/0082883 to Kohno, the disclosure of which is incorporated herein by reference, describes an ultrasound endoscope having a separable head-top to facilitate maintenance.

Instead of using an elongate probe, it has been suggested to use a small video capsule which acquires images within the patient and passes the images to a control station outside the patient. U.S. Pat. No. 5,604,531 to Iddan et al., the disclosure of which is incorporated herein by reference, describes a stand alone video capsule for swallowing by a patient. U.S. Pat. No. 6,632,171 to Iddan et al., the disclosure of which is incorporated herein by reference, describes a clamp for insertion of the capsule into the patient, for example when swallowing is not an option. The stand alone video capsules are limited, however, in collecting biopsy samples and in navigation.

U.S. patent publication 2001/0051766 to Gazdzinski and U.S. Pat. No. 5,653,677 to Okada, the disclosures of both of which are incorporated herein by reference, describe endoscopes having detachable video capsules.

U.S. Pat. No. 6,916,286 to Kazakevich, the disclosure of which is incorporated herein by reference, describes an endoscope having a video unit rotatably mounted on the distal end of the endoscope.

These endoscopes are complex and may be difficult to sterilize.

As sterilization of endoscopes is relatively difficult, disposable sheaths which cover an endoscope are used to isolate the endoscope from the patient tissue, so as to avoid time-consuming cleaning and disinfection processes. In some cases it is desired to have one or more channels run along the endoscope. These channels may be used, for example, to pass tools and fluids (e.g., water, drugs, air) to body tissue and/or to remove fluids from the body (e.g., using suction). As the sheath should completely isolate the endoscope from the human tissue, such channels are generally attached to the sheath, and do not extend within the endoscope. This, however, enlarges the cross-section of the sheath-covered endoscope being inserted into the patient. Such a larger diameter may make the insertion of the endoscope more difficult or may prevent the insertion altogether. In addition, the loading of the endoscope into the sheath is a complex task, especially since it should be done in a sterile environment, or, at a minimum, a contaminant-free environment.

U.S. Pat. No. 5,892,630 to Broome, the disclosure of which is incorporated herein by reference, describes a disposable endoscope, which has a non-disposable optical portion at its proximal end. While this endoscope may solve the problem of sterilization, it may not provide an image of sufficient quality.

SUMMARY OF THE INVENTION

An aspect of some embodiments of the present invention relates to an endoscope formed of a disposable elongate probe and a non-disposable video capsule (referred to also as an imaging capsule) mounted along its length, possibly at its distal end. Optionally, the disposable elongate probe defines a compartment for receiving the video capsule in a manner which isolates the video capsule from body tissue. Alternatively or additionally, the video capsule has smooth and/or crevice-free outer surfaces and/or has other properties which allow easy reprocessing, e.g., disinfecting, cleaning and/or sterilizing.

The use of a disposable insertion tube of an elongate probe with a non-disposable video capsule allows using a mainly disposable endoscope, with a high quality and/or expensive imaging unit and possibly an expensive proximal articulation handle. Since the video unit is reusable, it can be of higher quality than the disposable units of the prior art.

The video capsule is optionally designed to allow fast mounting on the disposable elongate probe, for example by fitting into a respective compartment in the probe. Possibly, the video capsule is adapted to be mounted without use of tools, bonding material (e.g., glue, epoxy) and/or without use of screws. In some embodiments of the invention, the video capsule is designed to be mounted within less than half a minute or even less than ten seconds.

In some embodiments of the invention, the video capsule is mounted at a distal end of the probe, within less than 5 centimeters or even less than two centimeters from its distal tip. Alternatively, the capsule is mounted along the length of the probe, optionally within the distal half or distal third of its length.

The video capsule may be self contained with all the elements required for operation, such as a battery, transceiver, antenna and/or LEDs, or one or more of the elements may be located within the disposable elongate probe. Accordingly, in some embodiments of the invention, electrical wires connecting to the video capsule, for example to provide power or confer image data, do not extend along the length of the elongate probe. Furthermore, the elongate probe possibly does not have optical fibers running along its length.

Optionally, the video capsule is powered by a battery located within the video capsule. Alternatively or additionally, the video capsule is powered by an external power source using wireless energy coupling. Further alternatively or additionally, a battery is located along the length of the probe or in the handle of the probe and is connected through wires and/or a coupling port to the video capsule.

There is therefore provided in accordance with an exemplary embodiment of the invention, a method of examining internal body portions of patients, comprising providing an imaging capsule including an image capturing unit, mounting the imaging capsule on a distal end of a first elongate tube suitable for insertion into a body cavity, in a manner which prevents release of the imaging capsule from the first elongate tube within a body cavity, inserting the first elongate tube with the capsule mounted thereon into a patient, retracting the first elongate tube from the patient, separating the imaging capsule from the first elongate tube, disposing of the first elongate tube, mounting the imaging capsule on a second elongate tube; and inserting the second elongate tube with the imaging capsule mounted thereon into a patient.

Optionally, the first elongate tube has a length of at least 50 centimeters. Optionally, inserting the first elongate tube into a body cavity comprises inserting into the intestine of a patient. Optionally, mounting the imaging capsule on the distal end comprises mounting in a manner such that the imaging capsule is stationary relative to the distal end of the first elongate tube. Optionally, mounting the imaging capsule on the distal end comprises mounting such that the imaging capsule is isolated from the environment outside the tube.

Optionally, mounting the imaging capsule on the distal end comprises mounting in a compartment in the elongate tube. Optionally, mounting the imaging capsule on the distal end comprises mounting in a compartment in the elongate tube, such that the imaging capsule fills most of the compartment. Optionally, the compartment comprises a recess which receives only part of the imaging capsule. Optionally, mounting the imaging capsule on the distal end comprises mounting such that a distal end of the imaging capsule is less than 30 millimeters behind a distal tip of the elongate tube. Possibly, the method includes recharging a battery of the imaging capsule between insertions of the first and second elongate tubes into patients.

Possibly, the method includes cleaning the imaging capsule between insertions of the first and second elongate tubes into patients. Optionally, the imaging capsule is not sterilized between insertions of the first and second elongate tubes into patients. Possibly, the method includes repeating the mounting and inserting for at least five different insertions into one or more patients. Possibly, the method includes repeating the mounting and inserting at least three times in a single day.

Optionally, mounting the imaging capsule comprises mounting such that the imaging capsule forms electrical contact with an electrical port within the elongate tube. Optionally, mounting the imaging capsule comprises mounting so as to form a contact between a power supply outside of the imaging capsule and a unit within the imaging capsule utilizing power of the power supply. Optionally, mounting the imaging capsule comprises mounting such that a transmitter within the imaging capsule forms a contact with an antenna in the elongate tube.

Optionally, mounting the imaging capsule comprises mounting such that the imaging capsule forms electrical contact with wires leading along the elongate tube to a proximal end thereof. Optionally, mounting the imaging capsule on the distal end comprises mounting within the distal 20% of the length of the elongate tube. Optionally, the elongate tube comprises at least one working channel adapted to allow passage of fluid or surgical tools into the patient. Optionally, disposing of the elongate tube comprises disposing of the tube together with a handle used for deflecting the elongate tube. Possibly, the method includes using a same handle for deflecting the first and second elongate tubes. Optionally, the elongate tube is rigid or semi-rigid.

Optionally, mounting the imaging capsule comprises mounting without at least one of screws and bonding material. Optionally, mounting the imaging capsule comprises mounting without use of screws. Optionally, mounting the imaging capsule comprises mounting without use of a bonding material.

There is further provided in accordance with an exemplary embodiment of the invention, an endoscope, comprising an optical imaging capsule including an optical image capturing unit; and an elongate tube, having a distal end adapted for insertion into a body cavity, and adapted to receive the imaging capsule at a position in its distal half in a manner which prevents detachment of the capsule from the elongate tube while a distal end of the elongate tube is in a body cavity, but allows release of the capsule from the elongate tube, when the tube is not in the body cavity, wherein the elongate tube does not have power wires extending from a proximal point of the insertion tube to the position for receiving the imaging capsule, which operably connect to the imaging capsule. Optionally, the optical imaging capsule includes a battery. Optionally, the optical imaging capsule includes a port adapted to connect to a respective port in the elongate tube. Optionally, the elongate tube defines a compartment adapted to receive the capsule, such that a distal wall of the elongate tube separates the capsule from tissue distal to the elongate tube. Optionally, the elongate tube defines a compartment adapted to receive the capsule, such that the elongate tube entirely surrounds the capsule.

Optionally, the elongate tube does not have electrical wires extending from a proximal point of the insertion tube to the position for receiving the imaging capsule.

There is further provided in accordance with an exemplary embodiment of the invention, an endoscope, comprising an optical imaging capsule including an optical image capturing unit; and an elongate tube, having a distal end adapted for insertion into a body cavity, and adapted to receive the imaging capsule at a position in its distal half in a manner which prevents detachment of the capsule from the elongate tube while a distal end of the elongate tube is in a body cavity, without requiring at least one of screws and bonding material, but allows release of the capsule from the elongate tube, when the tube is not in the body cavity.

Optionally, the elongate tube is adapted to receive the imaging capsule in a manner which prevents detachment without use of screws.

Optionally, the elongate tube is adapted to receive the imaging capsule in a manner which prevents detachment without use of bonding material.

Optionally, the elongate tube is adapted to removably receive the imaging capsule at its distal end in a manner which prevents movement of the capsule relative to the elongate tube while a distal end of the elongate tube is in a body cavity.

Optionally, the elongate tube does not include wires which are adapted to operably connect the imaging capsule to a power source at a proximal end of the tube.

Optionally, the elongate tube defines a recess adapted to receive the capsule, such that the capsule occupies at least 90% of the volume of the recess.

Optionally, the capsule can be mounted onto the elongate tube within less than 15 seconds. Optionally, the elongate tube is adapted to receive the capsule in a manner which allows removal of the capsule and use in a different elongate tube in a different patient, without sterilization of the capsule. Optionally, the imaging capsule is adapted to be mounted on the elongate tube without use of tools. Optionally, the elongate tube comprises a recess adapted to partially receive the imaging capsule. Optionally, the elongate tube comprises a recess adapted to receive the entire imaging capsule.

There is further provided in accordance with an exemplary embodiment of the invention, an endoscope, comprising an imaging capsule including, an optical image capturing unit and at least one of a LED, a battery and a wireless transmission unit adapted to operate in conjunction with the image capturing unit and an elongate tube adapted for insertion into a body cavity, and adapted to removably receive the imaging capsule at its distal end in a manner which prevents movement of the capsule relative to the elongate tube while a distal end of the elongate tube is in a body cavity. Optionally, the imaging capsule is connected to the elongate tube without any screws. Optionally, the imaging capsule does not have parts that extend proximally beyond the distal half of the elongate tube. Optionally, the imaging capsule comprises at least one LED arranged to illuminate an area imaged by the image capturing unit.

Optionally, the imaging capsule comprises at least one battery arranged to power the image capturing unit. Optionally, the imaging capsule comprises at least one wireless transmission unit. Optionally, the imaging capsule has a shape of a section of a cylinder.

Optionally, the imaging capsule does not include means for self navigation within a patient. Optionally, the imaging capsule has at least one external surface which is not adapted for contact with internal body tissue. Optionally, the endoscope does not include an optical fiber running along its length. Optionally, the elongate tube defines a recess at its distal end, covering less than the entire cross section of the distal end, adapted to removably receive the imaging capsule in a manner which prevents release of the capsule from the elongate tube while a distal end of the elongate tube is in a body cavity.

There is further provided in accordance with an exemplary embodiment of the invention, a disposable elongate probe for invasive medical procedures, comprising an elongate tube adapted for insertion into a body cavity, a proximal handle, at least one working channel extending along the elongate tube, at least one steering control allowing manipulation of a direction of the elongate tube from the proximal handle and at least one compartment at a distal portion of the elongate tube, adapted to receive an imaging capsule in a manner which prevents its release while the elongate tube is within a patient, but allows mounting of the capsule in the compartment without use of at least one of screws, tools and a bonding material.

There is further provided in accordance with an exemplary embodiment of the invention, an imaging capsule for use with a disposable elongate probe, comprising a housing having at least one outer surface not suitable for movement within a body cavity while contacting body tissue, an optical image capturing unit within the housing and at least one electrical unit adapted to operate in conjunction with the image capturing unit.

Optionally, the imaging capsule includes a port adapted for electrical contact with a respective port in the elongate probe. Optionally, the imaging capsule includes a wireless transmitter adapted to transmit images acquired by the image capturing unit.

BRIEF DESCRIPTION OF THE DRAWINGS

Exemplary non-limiting embodiments of the invention will be described with reference to the following description of the embodiments, in conjunction with the figures. Identical structures, elements or parts which appear in more than one figure are preferably labeled with a same or similar number in all the figures in which they appear, and in which:

FIG. 1 is a schematic illustration of an endoscope system, in accordance with an exemplary embodiment of the present invention;

FIG. 2A is an enlarged view of a distal end of an insertion tube of the endoscope of FIG. 1, in accordance with an exemplary embodiment of the invention;

DETAILED DESCRIPTION OF EXEMPLARY EMBODIMENTS

Figure 2B:
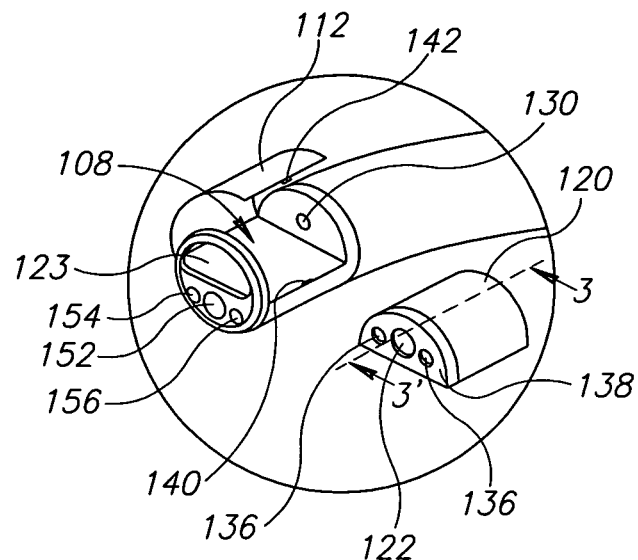
FIG. 2B is an enlarged view of a distal end of the insertion tube of FIG. 2A, in which a video capsule is outside a respective compartment in the distal end, in accordance with an exemplary embodiment of the invention.

FIG. 1 is a schematic illustration of an endoscope system 100, in accordance with an exemplary embodiment of the present invention. System 100 optionally includes a disposable elongate insertion tube 102 having a handle 104 carrying manipulation controls 106, an optionally adjustable distal end 109 and a control station 110, for example including a portable computer.

Endoscope system 100 may be used for substantially any endoscopic procedure and the details (e.g., size, shape, elements included) of insertion tube 102, handle 104 and the other parts of system 100 are selected according to its task. In the following description an exemplary endoscope for examination of the intestine, is described.

Insertion Tube

Insertion tube 102 optionally includes an articulation mechanism, for example including cables, which allows deflection control of distal end 109 thereof, from handle 104. In some embodiments of the invention, the articulation mechanism allows four-way deflection of distal end 109. Alternatively, the articulation mechanism allows deflection in fewer directions or in more directions (e.g., in 8 directions), possibly in all directions. In an exemplary embodiment of the invention, the deflection mechanism is in accordance with any of the embodiments and/or combinations of details in U.S. Pat. No. 5,667,476 to Frassica et al., U.S. Pat. No. 6,740,030 to Martone et al. and/or U.S. Pat. No. 5,704,898 to Kokish, the disclosures of all of these patents are incorporated herein by reference.

Insertion tube 102 optionally has an outer diameter greater than 2 millimeters or even greater than 5 millimeters, depending on the tasks and/or anatomy for which it is planned. Possibly, insertion tube 102 has a diameter of less than 14 millimeters, less than 10 millimeters or even less than 7 millimeters. In an exemplary embodiment of the invention, insertion tube 102 has an outer diameter of about 9 mm. Insertion tube 102 may have substantially any length, according to the task for which endoscope system 100 is designed, for example a length greater than 20 centimeters or even greater than 50 centimeters. Generally, for use in the intestine a length of at least 1.5 meters or even 2 meters, is used.

Insertion tube 102 may be rigid, semi-rigid with a flexible bending section or flexible. Optionally, if flexible, the insertion tube is sufficiently flexible to allow it to make at least a 90° bend or 150° bend with a radius of less than 20 mm, or even less than 10 mm, for example so that it can negotiate the turns of the intestine. Optionally, in one or more directions, insertion tube 102 can be manipulated to form a 180° bend or even at least a 270° bend over a distance of less than 30 millimeters. Possibly, insertion tube 102 allows different extents of bending in different directions. In an exemplary embodiment of the invention, insertion tube 102 is deflectable over 180° in the up-down direction and over 160° in the left-right direction.

Capsule Compartment

FIGS. 2A and 2B show an enlarged view of distal end 109 of insertion tube 102, in accordance with an exemplary embodiment of the invention. A compartment 108 adapted to receive a video capsule 120 is defined at a distal end 109 of insertion tube 102. In FIG. 2A video capsule 120 is shown within compartment 108, with its upper wall and its cover 112 (described below) transparent so that its contents may be viewed. In FIG. 2B, video capsule 120 is shown with its upper wall opaque. The upper wall of video capsule 120 as well as its bottom wall, its other walls and the parts of insertion tube 102 may be transparent or opaque, as desired.

Compartment 108 and video capsule 120 are optionally sized and shaped so that video capsule 120 entirely fits into the compartment. A cover 112 optionally fits above video capsule 120 within compartment 108 and separates the video capsule from body tissue of the patient. In some embodiments, cover 112 forms a hermetic seal eliminating the need to disinfect or sterilize video capsule 120. In some embodiments of the invention, a rubber or other elastomeric lining is placed within compartment 108 in a manner which prevents body fluids from entering the compartment. Possibly, as illustrated in FIG. 2B, cover 112 includes a notch 142 and tube 102 has a respective slot 140, which together lock the compartment 108 in a manner which prevents opening within the patient. Alternatively or additionally, any other locking mechanism is used to keep compartment 108 closed while tube 102 is in a patient. In some embodiments of the invention, opening of compartment 108 to remove capsule 120 requires, under normal conditions, breaking at least a portion of tube 102 so that it cannot be reused in another patient.

In other embodiments of the invention, instead of compartment 108, a recess which only partially receives video capsule 120, is used. For example, the recess may be at the distal tip of the elongate tube 102. The recess optionally receives at least 10%, at least 20% or even at least 30% of the video capsule. It is noted, however, that the recess may receive less than 80% or even less than 50% of the video capsule.

In some embodiments of the invention, compartment 108 or any other recess is sized and/or shaped to receive capsule 120, such that when video capsule 120 is in the compartment it occupies most of the volume of the recess. Possibly, video capsule 120 occupies at least 70%, 80% or even at least 90% of the volume of the recess. In some embodiments of the invention, video capsule 120 occupies substantially the entire volume of the recess. Optionally, the recess is separated from the interior of insertion tube 102, such that openings leading to compartment 108 or other recess cannot be used to access elements of disposable insertion tube 102, such as elements of an articulation mechanism.

Video capsule 120 optionally tightly fits into compartment 108, so that it does not move, rotate or exit the compartment without human intervention and/or does not move within or exit compartment 108 while the distal end 109 of the insertion tube 102 is in the patient. Optionally, video capsule 120 has a non-symmetric shape, which prevents rotation within compartment 108 and/or incorrect placement by a physician. In an exemplary embodiment of the invention, video capsule 120 has a shape of a section of a cylinder, for example having a D shaped cross section. It is noted that since in some embodiments of the invention video capsule 120 does not come in contact with internal body tissue, video capsule 120 may have sharp or rough surfaces or any other surfaces which are not suitable for contacting internal human tissue. Furthermore, video capsule 120 optionally does not include means for self navigation within a patient.

As mentioned above, in some embodiments of the invention cover 112 prevents capsule 120 from exiting the compartment. Alternatively or additionally, any other method of securing video capsule 120 within compartment 108, is used, such as a magnet, one or more detents or undercuts with respective notches, an adhesive and/or a quarter turn fastener. In some embodiments of the invention, capsule 120 includes a threading on one of its sides and is screwed into a respective threading in the compartment. In some embodiments of the invention, in accordance with this alternative, cover 112 is absent, allowing faster insertion and removal of capsule 120.

Possibly, before inserting capsule 120 into compartment 108 it is covered by a disposable cover, which is disposed after use, thus simplifying the cleaning process between uses of capsule 120, or even eliminating the need to clean or disinfect capsule 120 between uses.

Further Details of Insertion Tube

A front window 123 optionally allows a clear view from video capsule 120 to tissue distal from insertion tube 102. Window 123 is possibly formed of an optically clear plastic, such as acrylic or polycarbonate with a thickness of, for example, between 0.01-1.0 millimeters. In some embodiments of the invention, front window 123 has an arrangement for cleaning the window from outside, as described in U.S. provisional patent application 60/763,267, filed Jan. 30, 2006, and titled "Controllable Colonscope" and/or in PCT application PCT/IL2007/000116, filed Jan. 30, 2007, the disclosures of which are incorporated herein by reference.

One or more channels optionally extend along insertion tube 102, from its distal end to handle 104. In an exemplary embodiment of the invention, insertion tube 102 includes a working channel 152, an air channel 154 and a water channel 156. It is noted, however, that the insertion tube may include channels for other purposes, may include fewer channels, no channels at all, or may include more than three or even more than five channels.

Compartment 108 optionally occupies less than the entire cross-section of elongate tube 102, optionally less than 70% of the area of the cross-section or even less than half the area of the cross-section. Thus, part of the cross-section remains unobstructed for passage of the working channels.

As mentioned above, compartment 108 is located, in some embodiments of the invention, close to the distal end 109 of elongate tube 102, for example within less than 4 centimeters, 2 centimeter or even less than 1 centimeter from the distal end of the elongate tube. Alternatively, compartment 108 may be located along the elongate tube, remote from the distal end, separated by at least 5 or even 8 centimeters from the distal end 109. In some embodiments of the invention, in accordance with this alternative, compartment 108 is located in the distal half or distal third of the length of elongate tube 102. In accordance with this alternative, camera 124 is oriented radially outward to acquire images along side insertion tube 102.

Video Capsule

Figure 3:
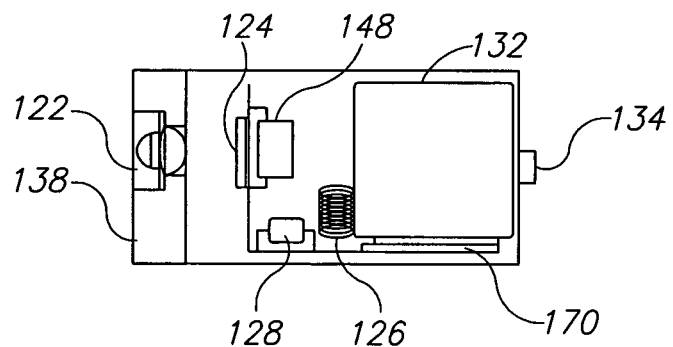
FIG. 3 is a sectional view of a video capsule, in accordance with an exemplary embodiment of the invention.

FIG. 3 is a sectional view of video capsule 120 along an axis corresponding to the length of insertion tube 102, in accordance with an exemplary embodiment of the invention. Video capsule 120 includes one or more optic lenses 122, one or more cameras 124 (e.g., a CCD or CMOS) or other image capturing devices, an optional antenna 126, an optional wireless transmitter 128 and an optional battery 132. A timing and/or control unit 148 optionally controls the operation of camera 124.

In some embodiments of the invention, video capsule 120 includes one or more LEDs, for example two LEDs 136 (FIG. 2B), which illuminate the area imaged by camera 124. In some embodiments of the invention, video capsule 120 includes at least four LEDs, at least six LEDs or even at least 10 LEDs. In some embodiments of the invention, one or more of the LEDs have corresponding lenses (not shown) which direct their light. In an exemplary embodiment of the invention, the lenses of LEDs 136 direct their light to a common point to which camera 124 is directed. Alternatively, the lenses of LEDs 136 direct the light of the LEDs in different directions so as to light a large area, in front, side and/or back directions. Possibly, the operation of LEDs 136 is controlled by control unit 148.

Possibly, a front panel 138 of video capsule 120 is transparent, allowing light from LEDs 136 to pass freely toward body tissue and return to camera 124. Alternatively, front panel 138 may be partially opaque, with separate transparent windows for LEDs 136 and camera 124, to prevent glare. Alternatively or additionally, window 123 of insertion tube 102 is replaced by an opaque wall which has within it a plurality of separate windows corresponding to respective elements (camera, LEDs) in capsule 120.

Battery

Battery 132 is optionally a rechargeable battery, which is recharged between uses of video capsule 120. In some embodiments of the invention, a physician may have two or more video capsules 120 which are used intermittently, one being reprocessed and/or having its battery recharged while the other is in use. Alternatively or additionally, the battery is easily removed from video capsule 120 for recharging. Alternatively or additionally to using rechargeable batteries, non-rechargeable batteries may be used. The batteries are optionally replaced after one or more medical procedures.

In some embodiments of the invention, the power of video capsule 120 is based solely on battery 132 and power wires do not extend along or within insertion tube 102. Alternatively or additionally, wires extending along insertion tube 102 connect a port 130 to a power source (not shown) at the proximal end of the insertion tube, for example through handle 104 and/or to a battery in handle 104. Video capsule 120 optionally includes a port 134 which connects to port 130 on tube 102 when video capsule 120 is placed in compartment 108. When video capsule 120 is inserted into compartment 108 contact is formed between ports 130 and 134 and power is supplied to video capsule 120. The power supplied through ports 130 and 134 may be in addition to battery 132, for example to charge the battery 132, or instead of the battery.

In other embodiments of the invention, insertion tube 102 or handle 104 carries within it a disposable battery (or batteries) connected to port 130.

Antenna

As mentioned above, in some embodiments of the invention, video capsule 120 includes an antenna 126 and transmitter 128 which are used to wirelessly transmit the acquired images from camera 124 to a control station 110 (FIG. 1). In some embodiments of the invention, video capsule 120 additionally includes a receiver, or transmitter 128 comprises a transceiver, such that control commands may be transmitted from control station 110 to video capsule 120, for example for adjusting the zoom of the camera, the rate of acquiring images and/or the resolution of the camera. Other operation parameters of video capsule 120, which may be controlled wirelessly include which LEDs 136 are operative and the direction to which camera 124 is aimed.

Alternatively or additionally to the antenna being within capsule 120, an antenna is included in a portion of tube 102 adjacent compartment 108, with an electrical connection to transmitter 128 (or a transceiver) in the video capsule 120, for example through ports 130 and 134. Further alternatively or additionally, acquired images are passed over wires extending along tube 102 to its proximal end. In some embodiments of the invention, the acquired images are transmitted in a modulated form (e.g., AM or FM) over the same wire used for providing power to capsule 120.

Further alternatively or additionally, video capsule 120 comprises a large memory 170 in which the acquired images are stored. For example, in some embodiments of the invention, transmitter 128 conveys low quality images to control station 110, while high quality images are stored in the memory and are viewed after the endoscope is removed from the patient. In other embodiments of the invention, transmitter 128 conveys high quality images and the images in the large memory (in those embodiments in which a large memory is included) serve as backups in case there are transmission problems. The backup can allow, for example, reducing the redundancy added to the signals for transmission. In some embodiments of the invention, a user can determine whether high quality or low quality images are transmitted.

Size and Rigidity

Video capsule 120 optionally has a length of less than 5 centimeters, less than 3 centimeters or even less than one centimeter, so as to minimize its effect on the flexibility of elongate tube 102, in those embodiments in which video capsule 120 is rigid. In some embodiments of the invention, video capsule 120 has a length of less than 10%, less than 5% or even less than 2% of the length of elongate tube 102. In an exemplary embodiment of the invention, elongate tube 102 is longer than a meter or even longer than a meter and a half, and the capsule has a length of less than 0.8% of the length of the elongate tube.

In some embodiments of the invention, video capsule 120 is rigid. Alternatively, the casing of capsule 120 and optionally some of its components, for example battery 132, are at least partially flexible, in order to allow the tip of insertion tube 102 high flexibility when capsule 120 is within it. Further alternatively or additionally, video capsule 120 is formed of a plurality of relatively rigid units connected through more flexible connectors.

Figure 4A:
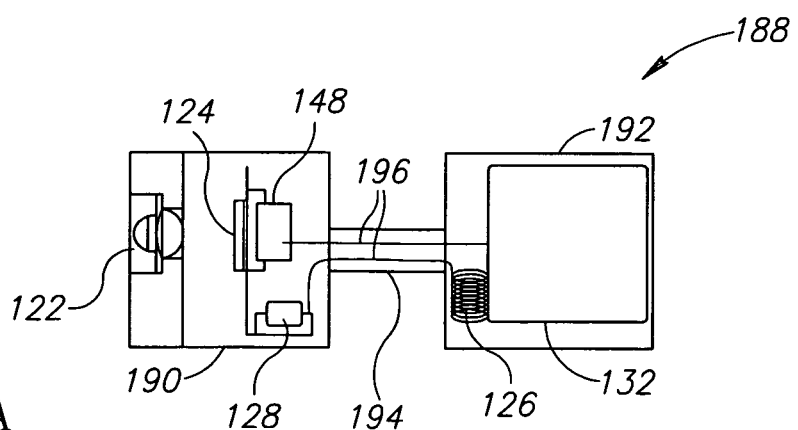
FIG. 4A is a sectional view of a video capsule, in accordance with another exemplary embodiment of the invention.

FIG. 4A is a sectional view of video capsule 188, in accordance with another exemplary embodiment of the invention. Video capsule 188 is formed of a video unit 190 and a power unit 192, which are connected to each other through a flexible connector 194. As shown, antenna 126 and battery 132 are located in power unit 192 and are connected to video unit 190 by wires 196 passing through flexible connector 194. It is noted, however, that any other distribution of the elements of the video capsule between units may be used. While video unit 190 is shown as being formed from two units, it may include more than two, more than three or even more than four units. Optionally, flexible connector 194 has a cross-section area of less than 50% or even less than 20% of the cross section areas of the units 190 and 192.

Other Details of Capsule

In some embodiments of the invention, video capsule 120 is activated by a control signal transmitted from control station 110. Alternatively or additionally, video capsule 120 has a switch which is manually activated by a physician when it is inserted into compartment 108. Further alternatively or additionally, video capsule 120 is operated by a switch which is automatically activated by a respective actuator on an inner wall of compartment 108. Further alternatively or additionally, any other activation method known in the art may be used.

Figure 4B:
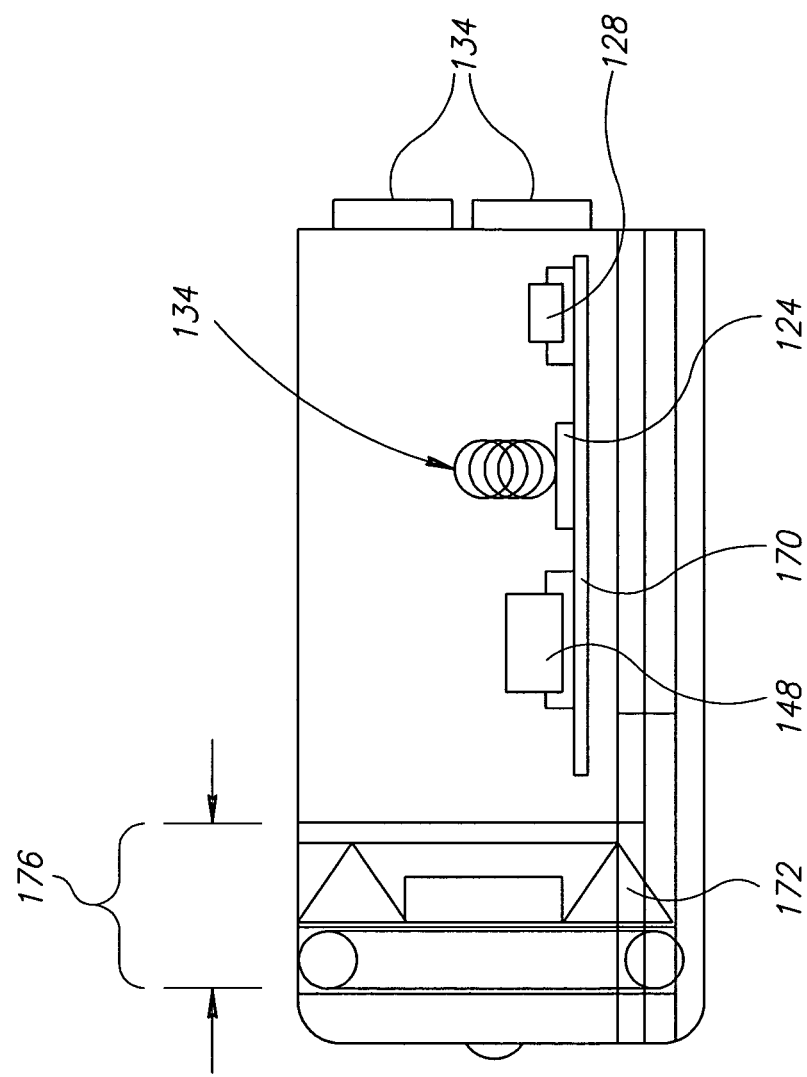
FIG. 4B is a sectional view of a video capsule, in accordance with still another exemplary embodiment of the invention.

FIG. 4B is a sectional view of video capsule 120, in accordance with still another exemplary embodiment of the invention. The embodiment of FIG. 4B illustrates a capsule 120 which does not carry a battery, but rather receives power through ports 134 using any of the methods discussed above. In some embodiments of the invention, the optics of camera 124 include a prism 172 and/or other optic element which provides for a wide field of view, possibly greater than 120°, greater than 150° or possibly even greater than 180°. The walls of capsule 120 at least in a section 176 and the corresponding walls of insertion tube 102 are optionally transparent around most or all the circumference of the capsule, in order to allow for acquiring images from the large field of view.

The above discussed details (e.g., shape, size, composition, elements) of video capsule 120 may be varied using any of the methods known in the art, such as using any of the embodiments and/or alternatives described in any of above mentioned U.S. Pat. Nos. 5,604,531, 6,632,171, 5,653,677 and 6,916,286 and/or U.S. patent publication 2001/0051766.

Usage

In preparation for a medical procedure, an insertion tube 102 is optionally removed from its sterile package and a video capsule is inserted into its compartment 108. After the medical procedure is completed, video capsule 120 is removed from compartment 108 and insertion tube 102, with or without handle 104, is discarded. Video capsule 120 is optionally reprocessed and prepared for a next medical procedure. A single video capsule may be limited to a specific number of uses, e.g., up to 50, up to 30 or even only up to 10, or may have an unlimited use as long as it works. Possibly, a single video capsule is used with at least five, at least ten or even more disposable elongate tubes. A single video capsule is possibly inserted into at least three, at least five or even at least eight insertion tubes 102 during a single day. The insertion of video capsule 120 into compartment 108 is optionally performed in a physicians clinic, less than an hour, less than half an hour, or even less than 10 minutes before the endoscopic procedure.

Alternatively or additionally, video capsule 120 may be limited to an amount of transmitted data or a number of times battery 132 is recharged. In some embodiments of the invention, transmitter 128 and/or a controller (e.g., 148) of video capsule 120 are configured to stop operating when a predetermined condition is fulfilled.

The reprocessing optionally includes disinfecting, cleaning and/or sterilizing video capsule 120. The level of cleaning and disinfecting may depend on the extent to which the interior of compartment 108 is isolated from its exterior. Alternatively or additionally, the extent of disinfecting may depend on the body organ into which tube 102 is inserted.

During the medical procedure, insertion tube 102 is inserted into the patient in accordance with the specific procedure and the anatomy. In some embodiments of the invention, at least 10 centimeters, 15 centimeters or even at least 20 or 30 centimeters of insertion tube 102 are inserted into the patient.

In some embodiments of the invention, the reprocessing includes replacing battery 132 or recharging the battery. Possibly, the reprocessing includes checking that capsule 120 is operative before its use. Optionally, a dedicated testing apparatus is used to test the module. The testing apparatus optionally includes a display unit which displays images to camera 124 and possibly a switch which causes capsule 120 to operate.

In some embodiments of the invention, video capsule 120 includes flat outer surfaces and/or is hermetically closed, in a manner which allows simple sterilization and/or disinfection.

Video capsule 120 and compartment 108 are optionally designed to allow fast insertion of the video capsule into the compartment and/or fast removal from the compartment. In some embodiments of the invention, the insertion and the removal each requires less than a minute, less than half a minute or even less than 10 seconds. Optionally, the insertion and/or removal of video capsule 120 from compartment 108 do not require use of tools and/or do not involve screwing or unscrewing of screws. Alternatively, a custom tool, designed specifically for manipulating video capsule 120 and/or handling compartment 108, e.g., a tool designed specifically for inserting video capsule 120 into compartment 108, is used. In other embodiments of the invention, one or more tools are required for inserting and/or removing video capsule 120. Possibly, the insertion and removal can be performed by an untrained person and do not require a technician. In some embodiments of the invention, the insertion and/or removal of video capsule 120 from compartment 108 do not require use of a bonding material (e.g., epoxy) or any other material, which is required to change its state, for example to harden from a liquid or semi-liquid state to a more solid state.

Insertion into Colon

Figure 5:
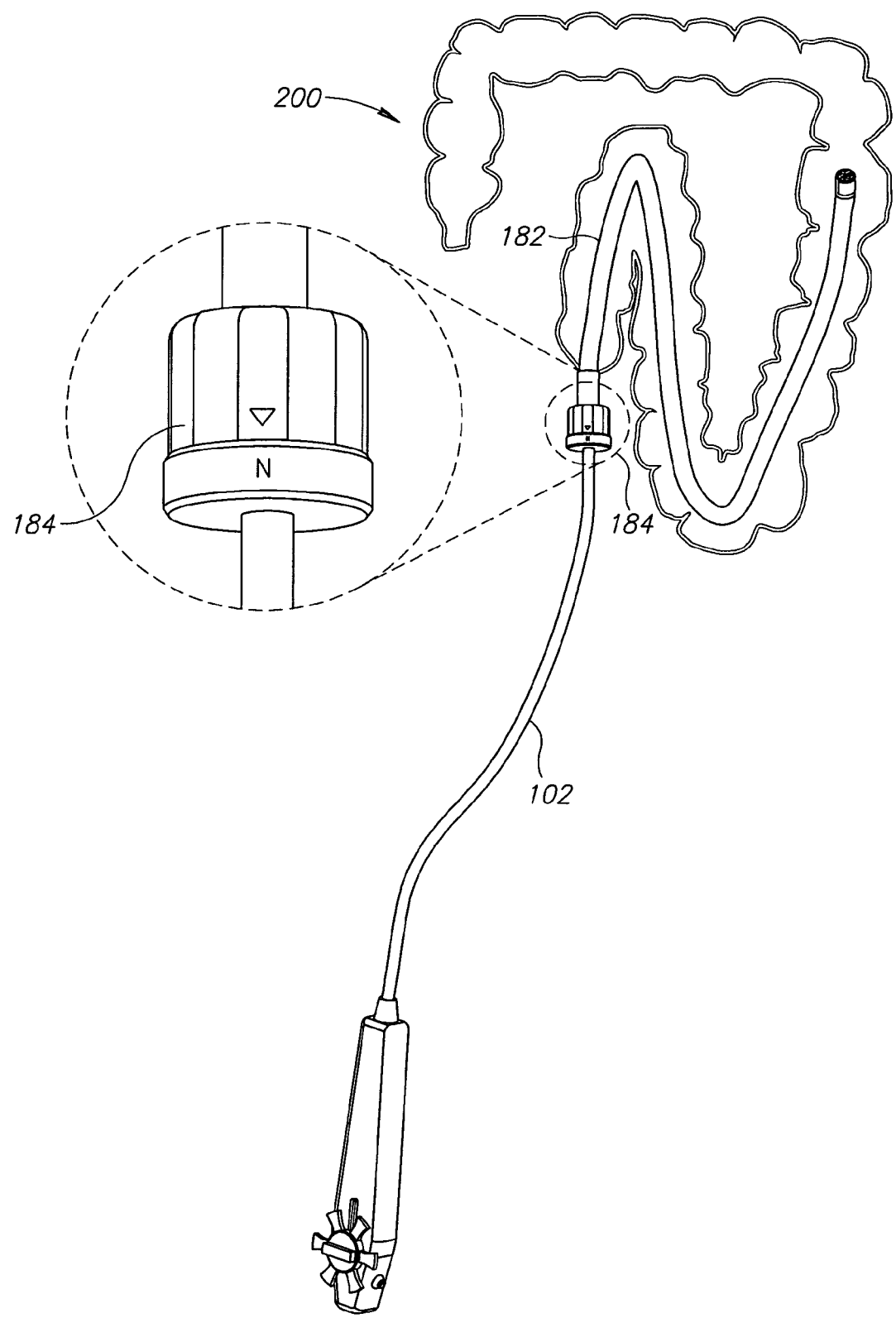
FIG. 5 is a schematic illustration of an endoscope partially within an intestine, in accordance with an exemplary embodiment of the invention.

FIG. 5 is a schematic illustration of insertion tube 102 introduced into a colon 200, in accordance with an exemplary embodiment of the invention. An outer sleeve 182, having a controllable stiffness, is optionally mounted over a distal portion of insertion tube 102. In some embodiments of the invention, a control knob 184 is used to control the stiffness of sleeve 182 and control a locking state between outer sleeve 182 and insertion tube 102. Optionally, outer sleeve 182 covers more than 25% or even more than 33% of the length of insertion tube 102. Alternatively or additionally, outer sleeve 182 has a length of less than 100 centimeters, less than 80 centimeters or even less than 70 cm. In an exemplary embodiment of the invention, outer sleeve has a length of about 65 cm.

Outer sleeve 182 optionally has an outer diameter greater than the outer diameter of insertion tube 102 by no more than 5 millimeters or even no more than 3 millimeters. Optionally, outer sleeve 182 has an outer diameter smaller than 16 millimeters, for example about 12 millimeters.

Figure 6:
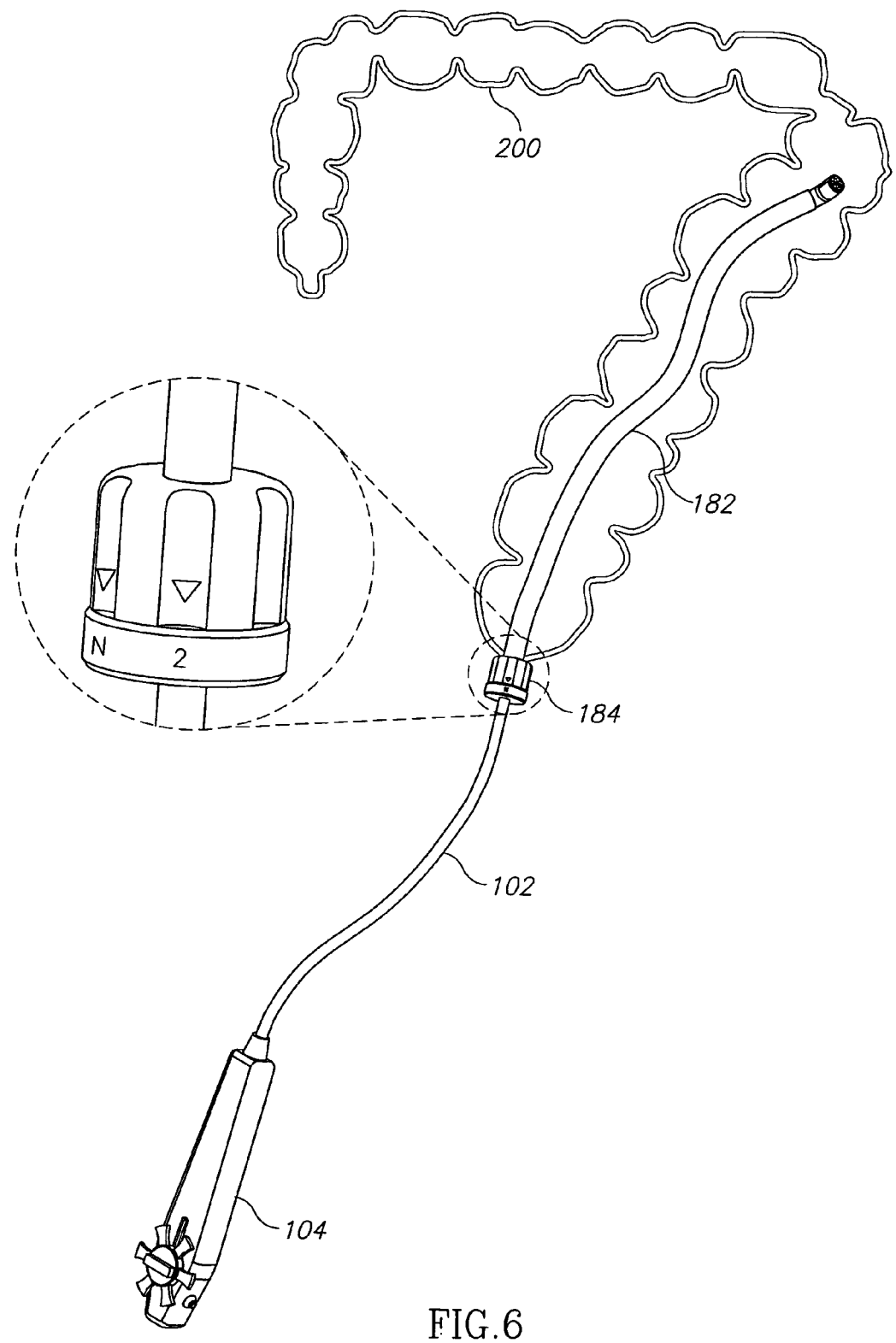
FIGS. 6 and 7 are schematic illustrations of an endoscope partially within an intestine with a stiff outer sleeve thereon, in accordance with an exemplary embodiment of the invention.
Figure 7:
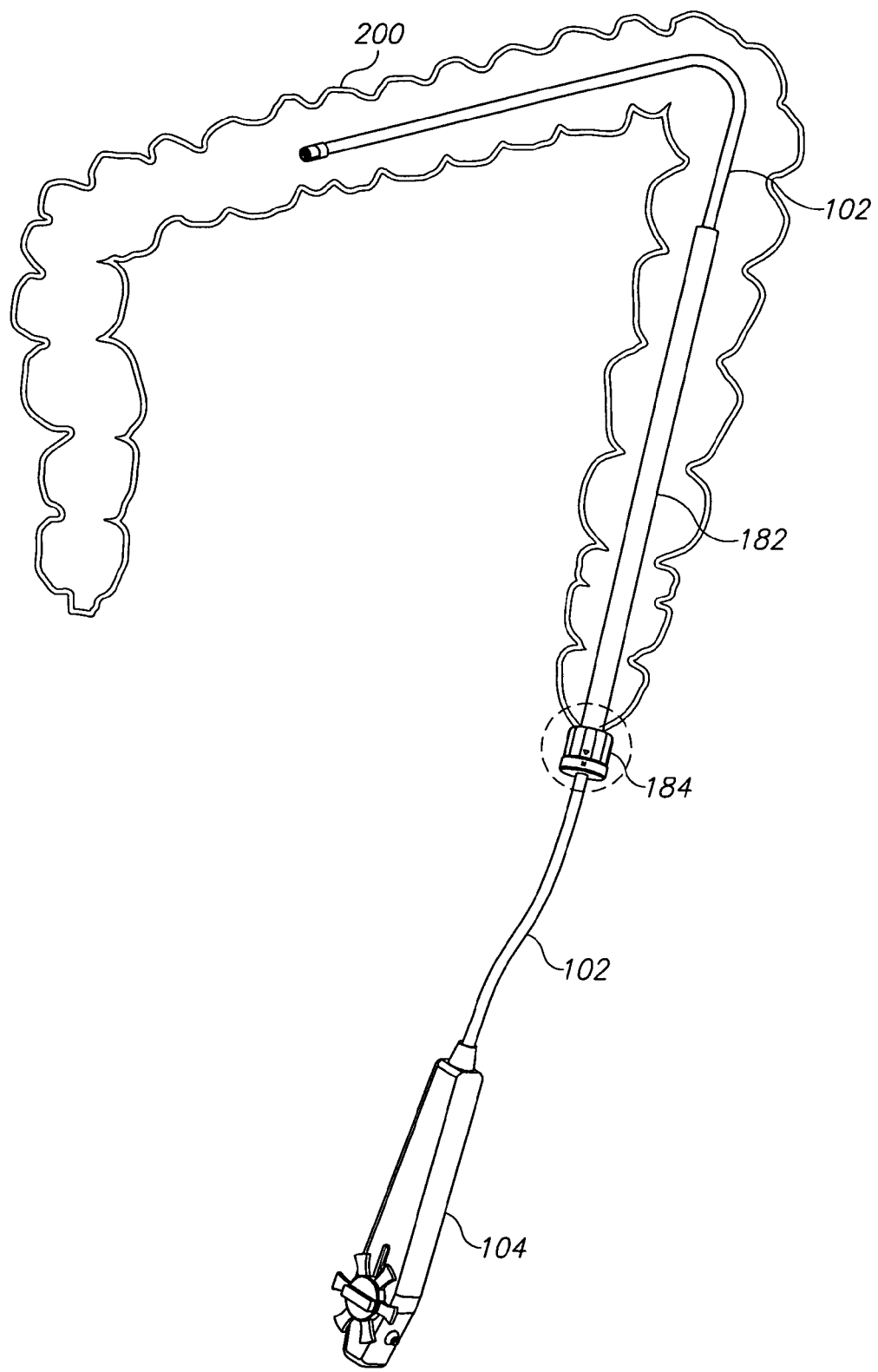

Initially, control knob 184 is set to lock outer sleeve 182 to insertion tube 102, while outer sleeve 182 has a relatively low rigidity, although optionally greater than the rigidity of insertion tube 102. In this state, insertion tube 102 with outer sleeve 182 on it, is inserted into colon 200. At any time, for example when nearly all (e.g., over 90%) of outer sleeve 182 is within the colon, control knob 184 may be turned, so as to gradually stiffen outer sleeve 182 and thus straighten insertion tube 102 and the portions of colon 200 in which outer sleeve 182 is located. FIG. 6 shows an intermediate stiffness state of outer sleeve 182. The stiffness is optionally further increased until outer sleeve 182 is completely straight, as shown in FIG. 7. The locking of insertion tube 102 to outer sleeve 182 is then optionally released and insertion tube 102 is pushed further into the colon.

The stiffness of outer sleeve 182 is optionally controlled using any method known in the art, such as according to any of the embodiments of U.S. Pat. No. 4,601,283 to Chikama, U.S. Pat. No. 4,893,613 to Hake, Japanese patent publication 6,237,886, U.S. Pat. No. 6,585,641 to Jordfald and/or U.S.

Pat. No. 6,761,685 to Adams et al., the disclosures of all of which patents are incorporated herein by reference.

The use of outer sleeve 182 reduces the chances and/or number of occurrences of insertion tube 102 folding over itself within the colon and/or enhances the control and eases the manipulation required by the user during the introduction of the insertion tube into the body. The straightening of the colon makes the access of insertion tube 102 therein simpler, as is known in the art.

Alternatively to an outer sleeve with a controllable stiffness, a relatively stiff sleeve is inserted over insertion tube 102, after it is inserted into the colon in order to straighten the colon and add to the stiffness of the insertion tube.

It is noted, that although the above description relates to insertion into the colon, system 100 may be used in other body cavities, for example in accessing the stomach through the esophagus and/or accessing the small intestine through the stomach and/or esophagus. It is noted that all details, dimensions and descriptions appearing on the figures are brought by way of non-limiting example and many other embodiments with different sizes and details are included in the scope of embodiments of the present invention. For example, a bronchoscope in accordance with an embodiment of the present invention may have a diameter of between about 4-5 millimeters, while an ear, nose, throat (ENT) endoscope may have a diameter of 3-4 millimeter.

Other apparatus designs may be used instead of those discussed above, for example any of the details in U.S. provisional application 60/763,267, filed Jan. 30, 2006, and titled "Controllable Colonscope", mentioned above. Although the above description relates mainly to the intestines, the embodiments of the present invention are not limited to any specific body organ and may be used for any body part, including the spine, thoraces, joint (e.g., knee) and bronchial. Depending on the specific body organ and/or task to be performed, the size, shape, structure (e.g., rigid, semi-rigid, flexible) and/or number or layout of working channels of insertion tube 102 is selected. Similarly, the size of capsule 120 and the apparatus it carries within may vary for different body organs and/or tasks.

While capsule 120 may be designed for only a single type of insertion tube, in some embodiments of the invention capsule 120 may be designed to operate with a plurality of different types of insertion tubes, for example differing in size (e.g., diameter), cross-sectional shape, number of channels and/or in the intended body organ for which they are designed. Similarly, a single type of insertion tube may be used, in some embodiments of the invention, with a plurality of different types of invention capsules, differing, for example, in the type of camera and/or optics (e.g., wide field, zoom) they employ.

It will be appreciated that the above-described methods may be varied in many ways, including, changing materials, sizes and shapes. For example, rather than camera 124 having a forward view, camera 124 may have a sideways view. Alternatively or additionally, video capsule 120 may include more than one camera, possibly more than three cameras, viewing different directions and/or operating with different light wavelengths. Alternatively or additionally, rather than including the camera lens 122 in capsule 120, the lens may be included in disposable insertion tube 102. This alternative may be used to make capsule 120 smaller.

It should also be appreciated that the above described description of methods and apparatus are to be interpreted as including apparatus for carrying out the methods, and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to".

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

The invention claimed is:

1. An endoscope, comprising:
   an optical imaging capsule including an optical image capturing unit;
   an elongate tube, having a distal end adapted for insertion into a body cavity, said elongate tube having a single receiving slot on a distal end thereof; and
   a compartment at said distal end adapted to receive the optical imaging capsule, the compartment including an openable and closable cover hingedly coupled to a side of said elongate tube, said cover including a notch thereon matingly and lockingly engageable with said single receiving slot, said cover configured to enclose said optical imaging capsule in its entirety and prevents detachment of the optical imaging capsule from the elongate tube while the optical imaging capsule is in a body cavity, but allows release of the optical imaging capsule from the elongate tube, when the elongate tube is not in the body cavity,
   wherein the elongate tube does not have power wires extending from a proximal point of the elongate tube to the position for receiving the optical imaging capsule, which operably connect to the optical imaging capsule, and
   wherein the optical imaging capsule is mounted into the compartment without screws and without setting bonding material.

2. An endoscope according to claim 1, wherein the optical imaging capsule includes a battery.

3. An endoscope according to claim 1, wherein the optical imaging capsule includes a port adapted to connect to a respective port in the elongate tube.

4. An endoscope according to claim 1, wherein a distal wall of the elongate tube separates the optical imaging capsule from tissue distal to the elongate tube.

5. An endoscope according to claim 1, wherein the elongate tube entirely surrounds the optical imaging capsule.

6. An endoscope according to claim 1, wherein the elongate tube does not have electrical wires extending from a proximal point of the elongate tube to the position for receiving the optical imaging capsule.

7. An endoscope according to claim 1, wherein the compartment is hermetically sealed.

8. An endoscope according to claim 1, wherein the compartment is adapted to removably receive the optical imaging capsule in a manner which enables removing the optical imaging capsule from the compartment after the elongate tube is out of the body cavity for reuse of the optical imaging capsule in a different elongate tube without sterilization of the optical imaging capsule.

9. An endoscope according to claim 1, wherein the compartment comprises a recess which receives only part of the optical imaging capsule.

10. An endoscope according to claim 1, wherein the elongated tube is adapted to receive the optical imaging capsule such that the optical imaging capsule is isolated from the environment outside the elongate tube.

11. An endoscope according to claim 1, wherein the elongate tube has a length of at least 50 centimeters.

12. An endoscope according to claim 1, wherein the elongated tube is adapted to receive the optical imaging capsule in a manner such that the optical imaging capsule is stationary relative to the distal end of the elongate tube.

13. An endoscope according to claim 1, wherein the elongated tube is adapted to receive the optical imaging capsule within the distal 20% of the length of the elongate tube.

14. An endoscope according to claim 1, wherein the elongate tube comprises at least one working channel adapted to allow passage of fluid or surgical tools into the body cavity.

15. An endoscope according to claim 1, wherein the elongate tube is rigid or semi-rigid.

16. An endoscope according to claim 1, wherein the endoscope further comprises a proximal end adapted to remain outside a body cavity.

17. An endoscope according to claim 1, wherein the elongate tube further includes an antenna adapted to form contact with a transmitter in the optical imaging capsule.

18. An endoscope according to claim 1, wherein the optical imaging capsule further includes a receiver for receiving control commands and controlling operation of the optical imaging capsule.

19. An endoscope according to claim 1, wherein the optical imaging capsule further includes a switch for activation of the optical imaging capsule when the optical imaging capsule is inserted into the compartment.

20. An endoscope according to claim 1, wherein the distal end of the elongate tube ends in a distal tip, and wherein the cover is positioned at the distal end, distanced from the distal tip of the elongate tube.

21. An endoscope according to claim 20, wherein the distal tip comprises a window through which the imaging capsule captures images.

22. An endoscope according to claim 1, wherein the cover remains attached to the elongated tube when opened.

23. An endoscope, comprising:
an optical imaging capsule including an optical image capturing unit;
an elongate tube, having a distal end adapted for insertion into a body cavity, said elongate tube having a single receiving slot on a distal end thereof; and
a compartment at said distal end adapted to receive the optical imaging capsule, the compartment including an openable and closable cover, said cover hingedly coupled on a side of said elongate tube and including a notch thereon matingly and lockingly engageable with said single receiving slot, said cover configured to enclose said optical imaging capsule in its entirety and prevents detachment of the optical imaging capsule from the elongate tube while a distal end of the elongate tube is in a body cavity, without requiring screws and bonding material, but allows release of the optical imaging capsule from the elongate tube, when the elongate tube is not in the body cavity.

24. An endoscope according to claim 23, wherein the endoscope further comprises a proximal end adapted to remain outside a body cavity.

25. An endoscope according to claim 23, wherein the elongate tube further includes an antenna adapted to form contact with a transmitter in the optical imaging capsule.

26. An endoscope according to claim 23, wherein the optical imaging capsule further includes a receiver for receiving control commands and controlling operation of the optical imaging capsule.

27. An endoscope according to claim 23, wherein the optical imaging capsule further includes a switch for activation of the optical imaging capsule when the optical imaging capsule is inserted into the compartment.

28. An endoscope according to claim 23, wherein the distal end of the elongate tube ends in a distal tip, and wherein the cover is positioned at the distal end, distanced from the distal tip of the elongate tube.

29. An endoscope according to claim 28, wherein the distal tip comprises a window through which the imaging capsule captures images.

30. An endoscope according to claim 23, wherein the cover remains attached to the elongated tube when opened.

31. An endoscope, comprising:
an imaging capsule including:
an optical image capturing unit; and
at least one of a LED, a battery and a wireless transmission unit adapted to operate in conjunction with the optical image capturing unit; and
an elongate tube comprising a distal end ending in a distal tip, the distal end adapted for insertion into a body cavity, said elongate tube including a single receiving slot thereon and including a compartment adapted to removably receive the imaging capsule, the compartment including an openable and closable cover at the distal end, distanced from the distal tip, said cover hingedly coupled to a side of said elongate tube including a notch thereon matingly and lockingly engageable with said single receiving slot, said cover configured to enclose said optical imaging capsule in its entirety and prevents movement of the imaging capsule relative to the elongate tube while a distal end of the elongate tube is in a body cavity.

32. An endoscope according to claim 31, wherein the endoscope further comprises a proximal end adapted to remain outside a body cavity.

33. An endoscope according to claim 31, wherein the elongate tube further includes an antenna adapted to form contact with the wireless transmission unit.

34. An endoscope according to claim 31, wherein the imaging capsule further includes a receiver for receiving control commands and controlling operation of the imaging capsule.

35. An endoscope according to claim 31, wherein the imaging capsule further includes a switch for activation of the imaging capsule when the imaging capsule is inserted into the compartment.

36. An endoscope according to claim 31, wherein the distal tip comprises a window through which the imaging capsule captures images.

37. An endoscope according to claim 31, wherein the cover remains attached to the elongated tube when opened.

38. An endoscope according to claim 31, wherein the capsule is mounted into the compartment without screws and without setting bonding material.

* * * * *